United States Patent [19]

Torii et al.

[11] Patent Number: 4,891,369
[45] Date of Patent: Jan. 2, 1990

[54] 2β-SUBSTITUTED-METHYLPENICILLANIC ACID DERIVATIVES, AND SALTS AND ESTERS THEREOF

[75] Inventors: Sigeru Torii; Hideo Tanaka; Motoaki Tanaka, all of Okayama; Shozo Yamada, Honjyo; Akira Nakai, Okayama; Hisashi Ohbayashi; Tomoyasu Ohno, both of Honjyo, all of Japan

[73] Assignee: Taiho Pharmaceutical Company, Limited, Tokyo, Japan

[21] Appl. No.: 123,631

[22] Filed: Nov. 23, 1987

[30] Foreign Application Priority Data

Dec. 3, 1986 [JP] Japan .................... 61-289595
Jan. 14, 1987 [JP] Japan .................... 62-6759
Jun. 26, 1987 [JP] Japan .................... 62-160278
Aug. 11, 1987 [JP] Japan .................... 62-201536

[51] Int. Cl.$^4$ .................. C07D 499/00; A61K 31/425
[52] U.S. Cl. .................. 514/192; 514/195; 540/310
[58] Field of Search ............ 540/310; 514/192, 195

[56] References Cited

U.S. PATENT DOCUMENTS 4,529,592  7/1985  Micetich et al. ........... 424/114
4,562,073 12/1985  Micetich et al. ........... 424/114
4,668,514  5/1987  Mictich et al. ........... 540/310

FOREIGN PATENT DOCUMENTS 2157286A 10/1985 United Kingdom .

Primary Examiner—Nicholas S. Rizzo
Attorney, Agent, or Firm—Armstrong, Nikaido, Marmelstein, Kubovcik & Murray

[57] ABSTRACT

Disclosed are 2β-substituted-methylpenicillanic acid compounds of the formula

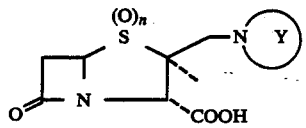

(I)

wherein n is 0, 1 or 2; and

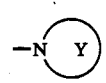

is monocyclic or bicyclic heterocyclic ring group which has 2 to 4 nitrogen atoms as hetero atom in its ring structure and which may be optionally substituted with alkyl, alkoxycarbonyl, phenyl, formyl or benzyloxycarbonyl optionally having alkyl, nitro or a halogen atom on the benzene ring, with the proviso that said heterocyclic ring group is not 1,2,3-triazol-1-yl; or salts or esters thereof.

These compounds are useful as β-lactamase inhibitor.

19 Claims, No Drawings

2β-SUBSTITUTED-METHYLPENICILLANIC ACID DERIVATIVES, AND SALTS AND ESTERS THEREOF

This invention relates to novel 2β-substututed methylpenicillanic acid derivatives, and salts and esters thereof which exert β-lactamase inhibitory effects and are useful as β-lactamase inhibitors.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve sufficient activities against some type of microorganisms owing to resistance of the microorganism to the β-lactam type antibiotics. The resistance thereof is usually attributable to β-lactamase produced by the microorganism, that is, an enzyme which acts to cleave the β-lactam ring, and thereby causes the antibiotic to lose its antimicrobial activity. Therefore, the action of β-lactamase must be eliminated or inhibited so as to enable the above β-lactam type antibiotic to exert its effect sufficiently. The elimination or inhibition of the β-lactamase activity can be achieved by β-lactamase inhibitors. When such a β-lactamase inhibitor is used with the β-lactam type antibiotic, the antimicrobial activity of the antibiotic can increase.

As an example of such β-lactamase inhibitor, there has been known YTR-830 having the following structure

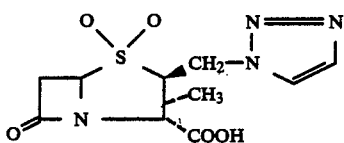

which is disclosed in U.S. Pat. No. 4,562,073.

However, the β-lactamase inhibitory effect of the above compound is still unsatisfactory, although superior to the other conventional compounds.

We conducted extensive research in view of the problem of the prior art mentioned-above, and found that certain 2β-substituted-methylpenicillanic acid derivatives and salts and esters thereof have excellent inhibitory activities against β-lactamase. The present invention was accomplished based on this novel findings.

This invention thus provides novel 2β-substituted-methylpenicillanic acid derivatives and salts and esters thereof.

The novel 2β-substituted methylpenicillanic acid derivative of the invention is represented by the following formula (I)

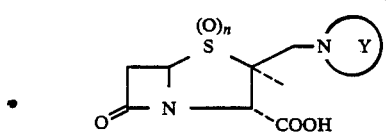

wherein n is 0, 1 or 2; and

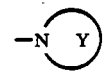

is monocyclic or bicyclic heterocyclic ring group which has 2 to 4 nitrogen atoms as hetero atom in its ring structure and which may be optionally substituted with alkyl, alkoxycarbonyl, phenyl, formyl or benzyloxycarbonyl optionally having alkyl, nitro or a halogen atom on the benzene ring, with the proviso that the heterocyclic ring group is not 1,2,3-triazol-1-yl.

Of the compounds of the invention, the compounds of the formula (I) wherein n is 2 is preferred since they exert stronger β-lactamase inhibitory activity. The compounds of the formula (I) wherein n is 0 or 1 are also useful as the intermediates for preparing the compounds of the formula (I) wherein n is 2. These intermediates, as will be described below, are oxidized with an oxidizing agent to give the compounds of the formula (I) wherein n is 2.

Throughout the specification and claims, the nitrogen-containing heterocyclic ring groups represented by

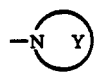

include 5-membered monocyclic heterocyclic ring groups having 2 to 4 nitrogen atoms in the ring structure, such as imidazolyl, pyrazolyl, tetrazolyl, 1,2,3-triazol-2-yl, which has the structural formula

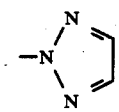

1,2,4-triazolyl and the like (other than 1,2,3-triazol-1-yl); and bicyclic heterocyclic ring groups, particularly those wherein a 5-membered heterocyclic group containing 2 or 3 nitrogen atoms in its ring structure is fused with a benzene ring, such as benzotriazolyl, benzimidazolyl, etc. These heterocyclic ring groups may optionally have 1 to 3, preferably 1 or 2, substituents selected from the group consisting of alkyl, alkoxycarbonyl, phenyl, formyl and benzyloxycarbonyl which may optionally have 1 to 3 substituents selected from the group consisting of $C_1$–$C_6$ alkyl, halogen and nitro on the benzene ring. In connection with the substituents of the heterocyclic ring groups, examples of alkyl groups are straight- or branched chain $C_1$–$C_6$ alkyl groups such as methyl, ethyl, propyl, isopropyl, butyl, sec-butyl, tertbutyl, pentyl, hexyl and the like. Examples of alkoxycarbonyl groups are $C_2$–$C_7$ alkoxycarbonyl groups such as methoxycarbonyl, ethoxycarbonyl, propyloxycarbonyl, isopropyloxycarbonyl, butoxycarbonyl, sec-butoxycarbonyl, tert-butoxycarbonyl, pentyloxycarbonyl and hexyloxycarbonyl and the like. Examples of benzyloxycarbonyl groups which may optionally have 1 to 3 substituents selected from the group consisting of $C_1$–$C_6$ alkyl, halogen and nitro on the benzene ring are benzyloxycarbonyl, o-nitrobenzyloxycarbonyl, p-nitrobenzyloxycarbonyl, m-nitrobenzyloxycarbonyl, p-chlorobenzyloxycarbonyl, m-chlorobenzyloxycarbonyl, o-fluorobenzyloxycarbonyl, p-bromobenzyloxycarbonyl, o-methylbenzyloxycarbonyl, p-ethylbenzyloxycarbonyl, m-propylbenzyloxycarbonyl, 4-nitro-2-methylbenzyloxycarbonyl, 2-nitro-4-ethylbenzyloxycarbonyl, 2,4-dinitrobenzyloxycarbonyl, 2,4,6-trinitrobenzyloxycarbonyl, 2,4-dimethylbenzyloxycarbonyl, 2,4,6-triethylbenzyloxycarbonyl and the like.

The esters of the penicillanic acid derivatives of the formula (I) are those wherein the penicillin carboxyl group is protected, and include both esters acceptable in the synthesis of pencillin compounds and pharmaceutically acceptable esters. Examples of the protective groups for forming such esters are lower alkyl groups such as methyl, ethyl, propyl, tert-butyl, pentyl and hexyl; lower alkoxymethyl groups such as methoxymethyl, ethoxymethyl, n-propyloxymethyl, iso-propyloxymethyl, iso-butoxymethyl and n-butoxymethyl; lower alkylcarbonyloxy-lower alkyl groups such as acetoxymethyl, propionyloxymethyl, n-butyryloxymethyl, iso-butyryloxymethyl, pivaloyloxymethyl, 1-acetoxyethyl, 1-pivaloyloxyethyl, 1-pivaloyloxypropyl and 1-propionyloxybutyl; ($C_{5-7}$ cycloalkyl)carbonyloxy-lower alkyl groups such as cyclopentylcarbonyloxymethyl and cyclohexylcarbonyloxymethyl; benzylcarbonyloxy-lower alkyl groups such as benzylcarbonyloxymethyl; and benzoyloxy-lower alkyl groups such as benzoyloxymethyl and benzoyloxyethyl. In the foregoing description and in the following description and throughout the specification and claims, the term "lower" used in conjunction with "alkyl" or "alkoxy" is intended to mean that the alkyl or alkoxy contains 1 to 6, preferably 1 to 4 carbon atoms. The alkyl or alkoxy groups may be in the form of either straight or branched chain. Other examples of penicillin carboxyl-protecting groups are 3-phthalidyl; lactone groups such as crotonolacton-4-yl and γ-butyrolacton-4-yl; halogenated lower alkyl groups which are substituted with 1 to 3 halogen atoms such as fluorine, chlorine, iodine and bromine, such as iodomethyl, fluoromethyl, 2,2-dibromoethyl and 2,2,2-trichloroethyl; methyl groups which are substituted with 1 to 2 phenyl groups optionally having lower alkoxy or nitro on the benzene ring, such as benzyl, p-methoxybenzyl, o-nitrobenzyl, p-nitrobenzyl and diphenylmethyl; tetrahydropyranyl; dimethylaminoethyl; dimethyl cholorosilyl; trichlorosilyl; tert-butylsilyl; (5-substituted or unsubstituted-2-oxo-1,3-dioxoden-4-yl)methyl groups such as (2-oxo-1,3-dioxoden-4-yl)methyl, (5-methyl-2-oxo-1,3-dioxoden-4-yl)methyl and (5-phenyl-2-oxo-1,3-dioxoden-4-yl)methyl; etc. Generally various ester-forming groups are used in the art to protect penicillin carboxyl groups in the synthesis of penicillin compounds. While it is difficult to determine which protecting groups for ester-forming should be used, the determination is done taking the following into consideration;

(1) the protecting group per se is sufficiently stable in the reaction, and
(2) the protecting group can be easily removed under the condition that does not permit cleavage of the β-lactam ring.

In the synthesis, the most commonly used protecting groups include a methyl group substituted by one or two phenyl groups optionally having lower alkoxy or nitro on the benzene ring.

A pharmaceutically acceptable ester means a non-toxic ester which can be easily hydrolyzed in vivo and which releases the corresponding free acid of the formula (I) in the blood or tissue of mammals including humans. Examples of the pharmaceutically acceptable ester are esters of lower alkylcarbonyloxy-lower alkyl, ($C_{5-7}$ cycloalkyl)carbonyloxy-lower alkyl, phthalidyl, γ-butyrolacton-4-yl, (5-substituted or unsubstituted-2-oxo-1,3-dioxoden-4-yl)methyl, etc.

The salt of the present invention means a non-toxic pharmaceutically acceptable salt which is capable of releasing the free acid of the formula (I) in vivo, and includes salts of alkali metals such as sodium, potassium and lithium, alkaline earth metals such as calcium and magnesium, organic amines such as cyclohexylamine, trimethylamine and diethanolamine, amino acids such as arginine and lysine, and anmonium.

The compound of the present invention represented by the formula (I), their salts and esters, when used with a known β-lactam antibiotic can increase the antimicrobial activity of the β-lactam antibiotic owing to the β-lactamase inhibitory effect, and is useful for treating infectious diseases in mammals including humans.

Therefore, the present invention also provides a pharmaceutical composition for treating bacterial infections in mammals which comprises (A) an effective amount of at least one compound of the foregoing formula (I) and a salt and ester thereof, (B) a β-lactam antibiotic and (C) a pharmaceutically acceptable carrier or excipient therefor.

The present invention also provides a pharmaceutical composition for inhibiting β-lactamase which comprises an effective amount of at least one of the compound of the formula (I) and a salt and ester thereof in combination with a pharmaceutically acceptable carrier or excipient therefor.

Examples of the antibiotics which can be used conjointly with the compound of the formula (I) and a salt and ester thereof according to the invention to thereby have their antimicrobial activity increased are β-lactam antibiotics displaying antimicrobial activities against various gram-positive and/or gram-negative bacteria, and include conventional penicillins such as ampicillin, amoxicillin, hetacillin, ciclacillin, mecillinam, carbenicillin, sulbenicillin, ticarcillin, piperacillin, apalcillin, methicillin, mezlocillin and pharmaceutically acceptable salts thereof; esters of penicillins such as bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cephadroxil and cephaloglycin and pharmaceutically acceptable salts thereof; and the like. The β-lactam antibiotics are usually used in an amount of about 0.1 to about 10 parts by weight, preferably about 0.2 to 5 parts by weight, per part by weight of the compound of the formula (I), salt or ester thereof according to the invention.

The compounds of the invention may be mixed with the β-lactam antibiotic to prepare the composition, which may be orally or parenterally administered. Also the compound of the invention and the β-lactam antibiotic are each made into compositions individually, and each composition may be administered separately.

The compounds of the invention are used to treat infections in mammal including humans by administering orally or pareterally. The compositions for oral administration are tablets, pills, capsules, granules, powders, syrups, troches, solutions, suspensions, etc. The compositions for parenteral administration are aqueous or suspending injections, injections which is dissolved in solvents on using, etc. for intravenous, intramuscular, subcutaneous and like administrations. Useful pharmaceutically acceptable carriers or excipients may be those commonly used in the art, and are non-toxic. Examples of the carriers or excipients include gelatin, lactose, starch, magnesium stearate, talc, vegetable or animal oil, polyalkylene glycol, etc. The carriers or excipient may be used with other usual additives such as diluents, binders, buffers and coating agents, thus preparing the above composition.

The daily dose of the composition can be appropriately determined and may depend on species, physical conditions, administration methods and many other factors. However, this judgement is well within the skill of the medical art. The amount is usually decided based on the $\beta$-lactamase inhibitory effective amount of the derivative of the formula (I). Preferably the daily dose is such that the total amount of the present compound and $\beta$-lactam antibiotic is about 1 to about 200 mg/Kg body weight for oral administration and about 1 to about 100 mg/Kg body weight for parenteral administration.

The penicillanic acid derivatives (I) can be prepared by the various processes shown in the following reaction scheme.

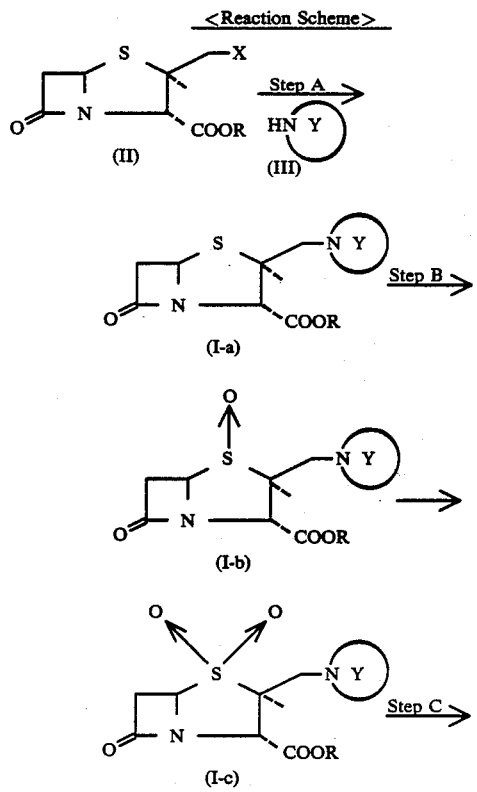

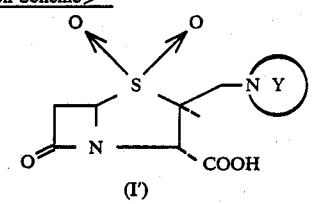

In the above formulas, X is chlorine atom or bromine atom, R represents a penicillin carboxyl protecting group, and

is as defined above.

Examples of the penicillin carboxyl protecting group represented by R include known groups such as any of those described in Japanese Unexamined Patent Publication No. 49-81380 and in "Cephalosporins and Penicillins, Chemistry and Biology" edited by H. E. Flynn (published in 1972 by Academic Press). Preferable examples of the group R are substituted or unsubstituted alkyl groups such as methyl, ethyl, propyl, butyl, tert-butyl and trichloroethyl; substituted or unsubstituted aralkyl groups such as benzyl, diphenylmethyl, trityl, p-nitrobenzyl and p-methoxybenzyl; acyloxyalkyl groups such as acetoxymethyl, acetoxyethyl, propionyloxyethyl, pivaloyloxymethyl, pivaloyloxyethyl, pivaloyloxypropyl, benzoyloxymethyl, benzoyloxyethyl, benzylcarbonyloxymethyl and cyclohexylcarbonyloxymethyl; alkoxyalkyl groups such as methoxymethyl, ethoxymethyl and benzyloxymethyl; and other groups such as tetrahydropyranyl, dimethylaminoethyl, dimethylchlorosilyl, trichlorosilyl and tert-butyldimethylsilyl.

Each step in the foregoing reaction scheme is described below in detail.

Step A

A penam derivative of the formula (II) is reacted with a heterocyclic compound of the formula

(III) in the presence or absence of a base to give a compound of the formula (I-a). The reaction is conducted in a suitable solvent by reacting the heterocyclic compound of the formula (III) with the known penam derivative of the formula (II) (U.S. Pat. No. 4,496,484) wherein the heterocyclic compound of the formula (III) is used in an amount of about 1 to 50 moles, preferably about 10 to 30 moles, per mole of the penam derivative of the formula (II), or alternatively by reacting the compound of the formula (III) with the derivative of the formula (II) in the presence of a base or a metal salt in a solvent wherein the base or metal salt is used in an amount of about 0.5 to 2 moles per mole of the derivative of the formula (II) and wherein the compound of the formula (III) is used in an amount of 1 to 10 moles, per mole of the derivative of the formula (II). Examples of the base or metal salt include alkali metal carbonates such as sodium hydrogencarbonate, potassium hydrogencarbonate and cesium carbonate, alkaline earth metal carbonates such as barium carbonate and calcium carbonate, carbonates of the copper group metals such as silver carbonate and copper carbonate, oxides of the copper group metals such as copper oxide and silver oxide, alkaline earth metal oxides such as magnesium oxide, calcium oxide and barium oxide, oxides of the zinc group metals such as zinc oxide and mercury oxide, oxides of the aluminum group metals such as aluminum oxide and thallium oxide, oxides of the carbon group metals such as tin oxide and zinc oxide, oxides of the iron group metals such as iron oxide, cobalt oxide and nickel oxide, hydroxides of the copper group metals such as copper hydroxide and silver hydroxide, organic amines such as pyridine, triethylamine and diisopropylethylamine, and anion exchange resin.

The solvent to be used is not particularly limited insofar as it does not adversely affect the reaction and includes, for example, acetonitrile, acetone, methyl ethyl ketone, dimethylformamide, nitromethane, tetrahydrofuran, dioxane, methanol, ethanol, methoxyethanol, dichloromethane and the like. These organic solvents are usable singly or at least two of them can be used in mixture. The organic solvent can be also used as mixed with water. The reaction is conducted usually at about 0° to about 80° C., preferably about 20° to 50° C. Generally the reaction is completed within 1 to 20 hours, and in many cases within 1 to 5 hours. After the reaction is completed, the desired compound may be subjected to the subsequent reaction as contained in the reaction miture or as isolated therefrom by the conventional method.

Step B

The compound of the formula (I-a) obtained in the above step A is oxidized, thereby giving a dioxide represented by the formula (I-c) via an intermediate of monoxide of the formula (I-b). The oxidation reaction employs common oxidizing agents such as permanganic acid, periodic acid, peracetic acid, trifluoroperacetic acid, perbenzoic acid and hydrogen peroxide. These oxidizing agents may be used optionally in excess, but may preferably be used in an amount of about 1 to about 5 moles per mole of the compound of the formula (I-a). The intermediate, i.e. monoxide of the formula (I-b), is prepared by suitably selecting the reaction conditions, the kind and amount of the oxidizing agent. The reaction is usually carried out in a suitable solvent.

Examples of the solvent can be any of those which do not affect the oxidation reaction such as dichloromethane, chloroform, carbon tetrachloride, pyridine, tetrahydrofuran, dioxane, acetone, formic acid, acetic acid, dimethylformamide, ethyl acetate and water. The reaction temperature is not particularly limited but generally about 0° to about 60° C.

The compounds of the formula (I-a), (I-b) or (I-c) thus obtained in the steps A and B may be the contemplated compound of the invention, i.e. the ester of the penicillanic acid derivative of the formula (I) to be hydrolyzed in vivo depending on the kind of the penicillin carboxyl protecting group represented by R in the compound. If desired, the compound is subjected to the de-esterification reaction described below in the step C to form the dioxide derivative of the formula (I') of the invention which, when required, is converted in the conventional manner to a pharmaceutically acceptable salt or to an ester thereof to be hydrolized in vivo.

Step C

The compound of the formula (I-c) is subjected to the de-esterification reaction as contained in, or as isolated from, the reaction mixture obtained in the step B to give the penicillanic acid derivative of the formula (I').

The de-esterification method which can be employed includes various conventional methods such as reduction, hydrolysis and the like which permit the conversion of a protected carboxyl group to a carboxyl group. Especially when the penicillin carboxyl-protecting group represented by R is trichloroethyl, benzyl, diphenylmethyl, p-nitrobenzyl or the like, the deesterification is advantageously conducted by reduction. When the protecting group is p-methoxybenzyl, tert-butyl, trityl, diphenylmethyl, methoxymethyl, tetrahydropyranyl, tert-butyldimethylsilyl or the like, the reaction is advantageously carried out using an acid.

Typical reduction can be effected by using a mixture of (a) a metal such as zinc or zinc-amalgam and/or a chromium salt such as chromium chloride or chromium acetate and (b) an acid such as formic acid or acetic acid, or can be catalytically performed. Examples of catalysts useful in the catalytic reduction are platinum, platinum oxide, palladium, palladium oxide, palladium-barium sulfate, palladium-calcium carbonate, palladium-carbon, nickel oxide, Raney-nickel and the like. Useful solvents are not particularly limited insofar as they do not adversely affect the reaction. Examples of preferable solvents include alcohols such as methanol and ethanol, ethers such as tetrahydrofuran and dioxane, esters such as ethyl acetate, fatty acids such as acetic acid, and a mixture of these organic solvents with water.

Examples of acids which can be used to convert the protected carboxyl group to carboxy group are lower fatty acids such as formic acid and acetic acid, trihaloacetic acids such as trichloroacetic acid and trifluoroacetic acid, hydrohalogenic acids such as hydrochloric acid and hydrofluoric acid, organic sulfonic acids such as p-toluenesulfonic acid or mixtures of these acids. When a liquid acid is used in the reaction involving the use of an acid, an additional solvent is not particularly required. However, it is possible to use a solvent which will not adversely affect the reaction, e.g., dimethylformamide, dichloromethane, chloroform, carbon tetrachloride, tetrahydrofuran, dioxane, acetone, etc.

The penicillin derivative of the formula (I') thus obtained in the form of free acid according to the invention can be converted to the desired pharmaceutically acceptable salt or ester by the salt-forming and/or esterification reaction conventionally employed in the art.

In preparing a compound wherein the ester residue is, for example, 3-phthalidyl, crotonolacton-4-yl, γ-butyrolacton-4-yl or the like, the penicillin derivative of the formula (I') can be esterified with a halide such as 3-halogenated phthalide, 4-halogenated crotonolactone and 4-halogenated γ-butyrolactone. Suitable halogen atoms of these halides are chlorine, bromine and iodine. The reaction is carried out by dissolving the salt of the penicillin derivative of the formula (I') in a suitable polar organic solvent such as N,N-dimethylformamide and adding an approximately equimolecular amount of the halide. The reaction temperature is generally about 0° to 80° C., preferably about 15° to 35° C. Examples of the salt of the penicillin derivatives used in the esterification reaction are salts of alkali metals such as sodium and potassium, salts of tertiary amines such as triethylamine, ethyldiisopropylamine, N-ethylpiperidine, N,N-dimethylaniline and N-methylmorpholine. After completion of the reaction, the desired compound can be easily isolated from the reaction product by a conventional method.

The contemplated compounds, the penicillin derivatives of the formula (I) or their pharmaceutically acceptable salts or esters obtained in the above steps are isolated and collected by the usual method after completion of the reaction, and, if desired, may be further purified by recrystallization, thin layer chromatography, column chromatography, or the like.

Given below are examples to illustrate the invention in detail.

EXAMPLE 1

Preparation of p-nitrobenzyl 2α-methyl-2β-(1,2,3-triazol-2-yl)methylpenam-3α-carboxylate A 741 mg quantity of p-nitrobenzyl 2β-chloromethyl-2α-methylpenam-3α-carboxylate, 276 mg of 1,2,3-triazole and 185 mg of sodium hydrogencarbonate were reacted in a mixture of 6 ml of acetone and 1.5 ml of water at 40° C. for 12 hours with heating and stirring. The acetone was distilled away under reduced pressure, and the residue was extracted with 15 ml of methylene chloride. The methylene chloride was then distilled away, and the resulting residue was purified by silica gel column chromatography (eluent: chloroform-acetone=19:1), giving as a first eluate 186 mg of p-nitrobenzyl 2α-methyl-2β-(1,2,3-triazol-2-yl)methylpenam-3α-carboxylate.

M.p.: 160°–161° C.
Infrared absorption spectrum (KBr) $\nu_{C=O}(cm^{-1})=1784, 1758$
Nuclear magnetic resonance spectrum (CDCl$_3$) δ (ppm)=1.25 (3H, s), 3.19 and 3.64 (each 1H, AB-X), 4.69 (2H, s), 5.25 (2H, AB), 5.34–5.41 (1H, m), 5.58 (1H, s), 7.67 (2H, s), 7.51 and 8.23 (each 2H, each d)

EXAMPLE 2

Preparation of p-nitrobenzyl 2α-methyl-2β-(1,2,3-triazol-2-yl)methylpenam-3α-carboxylate 1,1-dioxide A 110 mg quantity of p-nitrobenzyl 2α-methyl-2β-(1,2,3-triazol-2-yl)methylpenam-3α-carboxylate was dissolved in a mixture of 3.0 ml of acetone and 0.6 ml of water, and 0.6 ml of acetic acid was added to the solution. Then, 88 mg of potassium permanganate was added with stirring under ice-cooling, and the mixture was stirred at room temperature for 3 hours. After addition of 30% hydrogen peroxide until the reaction mixture became colorless, the mixture was extracted with 10 ml of methylene chloride. The residue obtained by distilling away the methylene chloride was subjected to silica gel column chromatography (eluent: chloroform-acetone=19:1), giving 115 mg of the title product in the form of a foam.

Infrared absorption spectrum (KBr) $\nu_{C=O}(cm^{-1})=1808, 1770$
Nuclear magnetic resonance spectrum (DMSO-d$_6$) δ (ppm)=1.24 (3H, s), 3.32 and 3.72 (each 1H, AB-X), 4.89 and 5.30 (each 1H, AB), 5.13 (1H, s), 5.13–5.23 (1H, m), 5.44 (2H, s), 7.86 (2H, s), 7.75 and 8.27 (each 2H, each d)

EXAMPLE 3

Preparation of p-nitrobenzyl 2α-methyl-2β-(1,2,3-triazol-2-yl)methylpenam-3α-carboxylate 1-oxide A 80 mg quantity of p-nitrobenzyl 2α-methyl-2β-(1,2,3-triazol-2-yl)methylpenam-3α-carboxylate was dissolved in 0.8 ml of methylene chloride. Then, 18.3 mg of formic acid and 0.05 ml of 30% aqueous hydrogen peroxide were added to the solution. The mixture was then stirred at room temperature for 4 hours. After the addition of 10 ml of water and 10 ml of methylene chloride, the methylene chloride layer was collected and concentrated under reduced pressure. The resulting residue was recrystallized from methanol, giving 67 mg of crystals.

M.p.: 155°–156° C. (decomp.)
Infrared absorption spectrum (KBr) $\nu_{C=O}(cm^{-1})=1796, 1762$
Nuclear magnetic resonance spectrum (CDCl$_3$) δ (ppm)=0.82 (3H, s), 3.43 (2H, d), 4.66 (1H, s), 4.91 (1H, t), 5.03 and 5.26 (each 1H, AB), 5.38 (2H, s), 7.68 (2H, s), 7.64 and 8.28 (each 2H, each d)

EXAMPLE 4

Preparation of sodium 2α-methyl-2β-(1,2,3-triazol-2-yl)methylpenam-3α-carboxylate 1,1-dioxide A 59 mg quantity of p-nitrobenzyl 2α-methyl-2β-(1,2,3-triazol-2-yl)methylpenam-3α-carboxylate 1,1-dioxide was hydrogenated at a low pressure and at room temperature in a mixture of 10 ml of ethyl acetate and 10 ml of water in the presence of 12 mg of sodium hydrogencarbonate and 60 mg of 5% palladium carbon. After two hours, the reaction mixture was filtered. The aqueous layer was separated and subjected to freeze-drying to give a crude sodium salt. This sodium salt was purified by column chromatographyl using MCI gel (product of Mitsubishi Chemical Corporation, Japan, CHP-20P). The eluate thus obtained was freeze-dried to give 34 mg of white powder.

M.p.: 185°–187° C. (decomp.)
Infrared absorption spectrum (KBr) $\nu_{C=O}$ (cm$^{-1}$)=1795, 1628
Nuclear magnetic resonance spectrum (D$_2$O) δ (ppm)=1.36 (3H, s) 3.47 and 3.68 (each 1H, AB-X), 4.47 (1H, s), 4.98–5.06 (1H, m), 5.23 and 5.30 (each 1H, each d), 7.85 (2H, s)

EXAMPLE 5

Preparation of p-nitrobenzyl 2α-methyl-2β-(tetrazol-1-yl)methylpenam-3α-carboxylate and p-nitrobenzyl 2α-methyl-2β-(tetrazol-2-yl)methylpenam-3α-carboxylate A mixture of 185 mg of p-nitrobenzyl 2β-chloromethyl-2α-methylpenam-3α-carboxylate, 50 mg of potassium hydrogencarbonate and 105 mg of tetrazole was stirred at 30° C. for 12 hours in a mixture of 3.75 ml of acetone and 1.25 ml of water. The reaction mixture was concentrated under reduced pressure and the concentrate was extracted with ethyl acetate. The extract was washed with an aqueous solution of sodium chloride, and dried over magnesium sulfate. The solvent was then distilled away under reduced pressure. The residue was subjected to silica gel column chromatography (eluent:

benzene-ethyl acetate=19:1) to give 71 mg of p-nitrobenzyl 2α-methyl-2β-(tetrazol-2-yl)methylpenam-3α-carboxylate as a first elutate.

Infrared absorption spectrum (CHCl$_3$) $\nu_{C=O}$ (cm$^{-1}$)=1780, 1750

Nuclear magnetic resonance spectrum (CDCl$_3$) δ (ppm)=1.29 (3H, s), 3.15 (1H, AB-X, J=2, 16 Hz), 3.67 (1H, AB-X, J=4, 16 Hz), 4.87 (2H, s), 5.23 (2H, s), 5.36 (1H, s), 5.30–5.45 (1H, m), 7.46 (2H, d), 8.16 (2H, d), 8.53 (1H, s)

A 66 mg quantity of p-nitrobenzyl 2α-methyl-2β-(tetrazol-1-yl)methllpenam-3α-carboxylate was subsequently obtained as a second eluate.

Infrared absorption spectrum (CHCl$_3$) $\nu_{C=O}$ (cm$^{-1}$)=1770, 1745

Nuclear magnetic resonance spectrum (CDCl$_3$) δ (ppm)=1.41 (3H, s), 3.17 (1H, AB-X, J=2, 16 Hz), 3.69 (1H, AB-X, J=4, 16 Hz), 4.67 (2H, s), 4.84 (1H, s), 5.24 (2H, s), 5.38 (1H, AB-X, J=2, 4 Hz), 7.43 (2H, d), 8.13 (2H, d), 8.82 (1H, s)

EXAMPLE 6

Preparation of p-nitrobenzyl 2β-(imidazol-1-yl)methyl-2α-methylpenam-3α-carboxylate A 185 mg quantity of p-nitrobenzyl 2β-chloromethyl-2α-methylpenam-3α-carboxylate, 138 mg of silver carbonate and 68 mg of imidazole were stirred at 30° C. for 5 hours in a mixture of 1.5 ml of acetonitrile and 0.5 ml of water. The reaction mixture was filtered on a Celite pad while being washed with ethyl acetate. The filtrate was washed with water and an aqueous solution of sodium chloride, and dried over magnesium sulfate. The solvent was distilled off under reduced pressure. The residue was purified by silica gel column chromatography (eluent: chloroform-acetone=19:1), giving 68 mg of p-nitrobenzyl 2β-(imidazol-1-yl)methyl-2α-methylpenam-3α-carboxylate.

Infrared absorption spectrum (CHCl$_3$) $\nu_{C=O}$ (cm$^{-1}$)=1773, 1750

Nuclear magnetic resonance spectrum (CDCl$_3$) δ (ppm)=1.37 (3H, s), 3.13 (1H, AB-X, J=2, 16 Hz), 3.69 (1H, AB-X, J=4, 16 Hz), 4.16 (2H, s), 4.69 (1H, s), 5.22 (2H, s), 5.36 (1H, AB-X, J=2, 4 Hz), 7.01 (2H, s), 7.45 (2H, d), 7.51 (1H, s), 8.16 (2H, d)

EXAMPLE 7

Preparation of p-nitrobenzyl 2α-methyl-2β-(1,2,4-triazol-1-yl)methylpenam-3α-carboxylate Following the general procedure of Example 6, 185 mg of p-nitrobenzyl 2β-chloromethyl-2α-methylpenam-3α-carboxylate was reacted with 70 mg of 1,2,4-triazole, giving 60 mg of p-nitrobenzyl 2α-methyl-2β-(1,2,4-triazol-1-yl)methylpenam-3α-carboxylate.

Infrared absorption spectrum (CHCl$_3$) $\nu_{C=O}$(cm$^{-1}$)=1770, 1745

Nuclear magnetic resonance spectrum (CDCl$_3$) δ (ppm) =1.39 (3H, s), 3.15 (1H, AB-X, J=2, 16 Hz), 3.70 (1H, AB-X, J=4, 16 Hz), 4.39 (2H, s), 5.14 (1H, s), 5.26 (2H, s), 5.43 (1H, AB-X, J=2, 4 Hz), 7.49 (2H, d), 7.96 (1H, s), 8.17 (1H, s), 8.20 (2H, d)

EXAMPLE 8

Preparation of p-nitrobenzyl 2β-(benzotriazol-1-yl)methyl-2α-methylpenam-3α-carboxylate Following the general procedure of Example 6, 185 mg of p-nitrobenzyl 2α-chloromethyl-2α-methylpenam-3α-carboxylate was reacted with 119 mg of benzotriazole to give 77 mg of p-nitrobenzyl 2β-(benzotriazol-1-yl)methyl-2α-methylpenam-3α-carboxylate.

Infrared absorption spectrum (CHCl$_3$) $\nu_{C=O}$ (cm$^{-1}$)=1775, 1750

Nuclear magnetic resonance spectrum (CDCl$_3$) δ (ppm)=1.43 (3H, s), 3.14 (1H, AB-X, J=2, 16 Hz), 3.68 (1H, AB-X, J=4, 16 Hz), 4.86 (2H, s), 5.20 (3H, s), 5.37 (1H, AB-X, J=2, 4 Hz), 7.30–8.30 (8H, m)

EXAMPLE 9

Preparation of p-nitrobenzyl 2α-methyl-2β-(1,2,4-triazol-1-yl)methylpenam-3α-carboxylate A 370 mg quantity of p-nitrobenzyl 2β-chloromethyl-2α-methylpenam-3α-carboxylate and 1.38 g of 1,2,4-triazole were reacted with stirring at 30° C. for 5 hours in a mixture of 3 ml of acetonitrile and 1 ml of water. The reaction mixture was diluted with ethyl acetate and filtered. The filtrate was washed with an aqueous sodium bicarbonate solution and an aqueous sodium chloride solution, and dried over magnesium sulfate. The solvent was distilled off under reduced pressure. The residue was purified by silica gel column chromatography (eluent: chloroform-acetone=19:1) to give 166 mg of p-nitrobenzyl 2α-methyl-2β-(1,2,4-triazol-1-yl)methylpenam-3α-carboxylate.

The infrared absorption spectrum and nuclear magnetic resonance spectrum of this compound were identical with those of the compound obtained in Example 7.

EXAMPLE 10

Preparation of p-nitrobenzyl 2α-methyl-2β-(pyrazol-1-yl)methylpenam-3α-carboxylate A 1.111 g quantity of p-nitrobenzyl 2β-chloromethyl-2α-methylpenam-3α-carboxylate, 3.06 g of pyrazole and 833 mg of anion-exchange resin (Diaion WA30, product of Mitsubishi Chemical Corporation, Japan) were reacted with stirring at 40° C. for one hour in a mixture of 9 ml of acetonitrile and 3 ml of water. The anion-exchange resin was filtered off, and the filtrate was separated after shaking with methylene chloride and water. The methylene chloride layer separated was dried over magnesium sulfate and the methylene chloride was distilled off under reduced pressure. The resulting residue was subjected to silica gel column chromatography (eluent: chloroform-acetone=19:1), giving 405 mg of p-nitrobenzyl 2α-methyl-2β-(pyrazol-1-yl)methylpenam-3α-carboxylate.

Infrared absorption spectrum (KBr) $\nu_{C=O}$(cm$^{-1}$)=1780, 1742

Nuclear magnetic resonance spectrum (CDCl$_3$) δ (ppm)=1.35 (3H, s), 3.17 (1H, AB-X, J=2, 16 Hz), 3.64 (1H, AB-X, J=4, 16 Hz), 4.35 (2H, s), 5.26 (2H, s), 5.29 (1H, s), 5.35–5.41 (1H, m), 6.26–6.30 (1H, m), 7.46–7.56 (4H, m), 8.21 (2H, d)

EXAMPLE 11

Preparation of p-nitrobenzyl 2α-methyl-2β-(pyrazol-1-yl)methylpenam-3α-carboxylate 1-oxide A mixture of 22 mg of p-nitrobenzyl 2α-methyl-2β-(pyrazol-1-yl)methylpenam-3α-carboxylate, 13 mg of 30% hydrogen peroxide solution and 10 mg of formic acid was stirred at room temperature for 4 hours in 0.3 ml of methylene chloride. The mixture was washed with water, and dried over magnesium sulfate. The solvent was distilled off under reduced pressure. The residue was purified by silica gel column chromatography (eluent: chloroform-acetone=19:1) to give 20 mg of p-nitrobenzyl 2α-methyl-2β-(pyrazol-1-yl)methylpenam-3α-carboxylate 1-oxide.

Infrared absorption spectrum (CHCl$_3$) $\nu_{C=O}$ (cm$^{-1}$)=1802, 1748

Nuclear magnetic resonance spectrum (CDCl$_3$) δ (ppm)=1.00 (3H, s), 3.39–3.40 (2H, m), 4.52–5.06 (4H, m), 5.36 (2H, s), 6.28–6.33 (1H, m), 7.52–7.65 (4H, m), 8.27 (2H, d)

EXAMPLE 12

Preparation of p-nitrobenzyl 2α-methyl-2β-(pyrazol-1-yl)methylpenam-3α-carboxylate 1,1-dioxide A mixture of 300 mg of p-nitrobenzyl 2α-methyl-2β-(pyrazol-1-yl)methylpenam-3α-carboxylate and 552 mg of 70% perbenzoic acid was stirred at 40° C. for 4 hours in 3 ml of methylene chloride. The mixture was washed with an aqueous sodium bicarbonate solution and dried over magnesium sulfate. The solvent was distilled off under reduced pressure. The residue was purified by silica gel column chromatography (eluent: chloroform-acetone=19:1) to give 276 mg of p-nitrobenzyl 2α-methyl-2β-(pyrazol-1-yl)methylpenam-3α-carboxylate 1,1-dioxide.

Infrared absorption spectrum (CHCl$_3$) $\nu_{C=O}$ (cm$^{-1}$)=1802, 1760

Nuclear magnetic resonance spectrum (CDCl$_3$) δ (ppm)=1.31 (3H, s), 3.50–3.53 (2H, m), 4.55–4.96 (4H, m), 5.31 (2H, s), 6.27–6.32 (1H, m), 7.35–7.62 (4H, m), 8.24 (2H, d)

EXAMPLE 13

Preparation of p-nitrobenzyl 2β-(imidazol-1-yl)methyl-2α-methylpenam-3α-carboxylate 1,1-dioxide A 1.04 g quantity of p-nitorbenzyl 2β-(imidazol-1-yl)methyl-2α-methylpenam-3α-carboxylate was dissolved in a mixture of 28 ml of acetone and 5.7 ml of water, and 5.7 ml of acetic acid was added thereto. Then, 830 mg of potassium permanganate was gradually added thereto with sirring under ice-cooling, and the resulting mixture was stirred at room temperature for 3 hours. Subsequently, 30% aqueous hydrogen peroxide was added to the reaction mixture until the mixture became colorless. After extraction with methylene chloride, the methylene chloride layer was dried over magnesium sulfate, and the solvent was distilled off under reduced pressure. The residue obtained was subjected to silica gel column chromataography (eluent: chloroform-acetone=5:1) to give 640 mg of p-nitrobenzyl 2β-(imidazol-1-yl)methyl-2α-methylpenam-3α-carboxylate 1,1-dioxide.

Infrared absorption spectrum (KBr) $\nu_{C=O}$ (cm$^{-1}$)=1808, 1770

Nuclear magnetic resonance spectrum (CDCl$_3$) δ (ppm)=1.29 (3H, s), 3.54–3.58 (2H, m), 4.38 and 4.76 (each 1H, AB, J=15 Hz), 4.52 (1H, s), 4.58–4.74 (1H, m), 6.98 (1H, s), 7.08 (1H, s), 7.47 (1H, s), 7.55 and 8.27 (each 2H, each d)

EXAMPLE 14

Preparation of sodium 2β-(imidazol-1-yl)methyl-2α-methylpenam-3α-carboxylate 1,1-dioxide A 640 mg quantity of p-nitrobenzyl 2β-(imidazol-1-yl)methyl-2α-methylpenam-3α-carboxylate 1,1-dioxide was hydrogenated at low pressure and at room temperature in a mixture of 50 ml of ethyl acetate and 50 ml of water using 320 mg of 10% palladium carbon and 123 mg of sodium hydrogencarbonate. After 2 hours, the palladium carbon was filtered off. The aqueous layer was separated from the filtrate, freeze-dried, and purified by MCI gel column chromatography. The eluate was freeze-dried to give 580 mg of the desired compound as a white powder.

Infrared absorption spectrum (KBr) $\nu_{C=O}$ (cm$^{-1}$)=1785, 1638

Nuclear magnetic resonance spectrum (CDCl$_3$) δ (ppm)=1.47 (3H, s), 3.47 (1H, AB-X, J=1.3, 16.7 Hz), 3.70 (1H, AB-X, J=4, 16.7 Hz), 4.39 (1H, s), 4.75 and 4.95 (each 1H, AB, J=17 Hz), 4.89–5.06 (1H, m), 6.80–7.40 (2H, broad), 7.60–8.00 (1H, broad)

EXAMPLE 15

Preparation of p-nitrobenzyl 2α-methyl-2β-(1,2,4-triazol-1-yl)methylpenam-3α-carboxylate 1,1-dioxide A 820 mg quantity of p-nitrobenzyl 2α-methyl-2β-(1,2,4-triazol-1-yl)methylpenam 3α-carboxylate was dissolved in a mixture of 22 ml of acetone and 4.5 ml of water, and 4.5 ml of acetic acid was added thereto. Then 645 mg of potassium permanganate was added thereto with stirring under ice-cooling, and the mixture was stirred at room temperature for 3 hours. Until the reaction mixture became colorless, 30% aqueous hydrogen peroxide was added. The mixture was extracted with methylene chloride. The methylene chloride layer was dried over magnesium sulfate, and the solvent was distilled away under reduced pressure. The residue was subjected to silica gel column chromatography (eluent: chloroform-acetone=19:1), giving 520 mg of p-nitrobenzyl 2α-methyl-2β-(1,2,4-triazol-1-yl)methylpenam-3α-carboxylate 1,1-dioxide.

Infrared absorption spectrum (KBr) $\nu_{C=O}$ (cm$^{-1}$)=1800, 1720

Nuclear magnetic resonance spectrum (CDCl$_3$) δ (ppm)=1.37 (3H, s), 3.54–3.58 (2H, m), 4.61–4.68 (1H, m), 4.72 and 4.85 (2H, AB, J=12 Hz), 4.77 (1H, s), 7.57 (2H, d), 7.96 (1H, s), 8.28 (2H, d), 8.30 (1H, s)

EXAMPLE 16

Preparation of sodium 2α-methyl-2β-(1,2,4-triazol-1-yl)methylpenam-3α-carboxylate 1,1-dioxide A 274 mg quantity of p-nitrobenzyl 2α-methyl-2β-(1,2,4-triazol-1-yl)methylpenam-3α-carboxylate 1,1-dioxide was hydrogenated at low pressure and at room temperature in a mixture of 40 ml of ethyl acetate and 40 ml of water using 140 mg of 10% palladium carbon and 53 mg of sodium hydrogencarbonate. After 2 hours, the palladium carbon was filtered off. The aqueous layer was separated from the filtrate, freeze-dried, and purified by MCI gel column chromatography. The eluate was freeze-dried to give 140 mg of the desired compound as a white powder.

Infrared absorption spectrum (KBr) $\nu_{C=O}$ (cm$^{-1}$)=1785, 1630

Nuclear magnetic resonance spectrum (CDCl$_3$) δ (ppm)=1.47 (3H, s), 3.51 (1H, AB-X, J=1.8, 16.7 Hz), 3.70 (1H, AB-X, J=4.2, 16.7 Hz), 4.50 (1H, s), 5.00 and 5.17 (2H, AB, J=15.4 Hz), 4.98–5.16 (1H, m), 8.14 (1H, s), 8.65 (1H, s)

EXAMPLE 17

Preparation of p-nitrobenzyl 2β-(4-methoxycarbonyl-5-methyl-1,2,3-triazol-2-yl)methyl-2α-methylpenam-3α-carboxylate A 185 mg of p-nitrobenzyl 2β-chloromethyl-2α-methylpenam-3α-carboxylate, 213 mg of 4-methoxycarbonyl-5-methyl-1,2,3-triazole and 50 mg of potassium hydrogencarbonate were added to 2 ml of a mixture of actonitrile and water (3:1), and the mixture was stirred at 40° C. for three hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent: benzene-ethyl acetate=19:1) to obtain 79 mg of p-nitrobenzyl 2β-(4-methoxycarbonyl-5-methyl-1,2,3-triazol-2-yl)methyl-2α-methylpenam-3α-carboxylate.

Infrared absorption spectrum (CHCl$_3$) $\nu_{C=O}$ (cm$^{-1}$)=1773, 1740, 1720

Nuclear magnetic resonance spectrum (CDCl$_3$) δ (ppm)=1.27 (3H, s), 2.46 (3H, s), 3.08 (1H, AB-X, J=2, 16 Hz), 3.61 (1H, AB-X, J=4, 16 Hz), 3.89 (3H, s), 4.60 (2H, s), 5.20 (2H, s), 5.29 (1H, AB-X, J=2, 4 Hz), 5.46 (1H, s), 7.41 (2H, d), 8.13 (2H, d)

EXAMPLE 18

Preparation of p-nitrobenzyl 2β-(4-methoxycarbonyl-1,2,3-triazol-2-yl)methyl-2α-methylpenam-3α-carboxylate A 185 mg quantity of p-nitrobenzyl 2β-chloromethyl-2α-methylpenam-3α-carboxylate, 190 mg of 4-methoxycarbonyl-1,2,3-triazole and 50 mg of potassium hydrogencarbonate were added to 5 ml of a mixture of acetone and water (3:1), and the mixture was stirred at 30° C. for three hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent: benzene-ethyl acetate=19:1) to obtain 81 mg of p-nitrobenzyl 2β-(4-methoxycarbonyl-1,2,3-triazol-2-yl)methyl-2α-methylpenam-3α-carboxylate.

Infrared absorption spectrum (CHCl$_3$) $\nu_{C=O}$ (cm$^{-1}$)=1780, 1740

Nuclear magnetic resonance spectrum (CDCl$_3$) δ (ppm)=1.28 (3H, s), 3.11 (1H, AB-X, J=2, 16 Hz), 3.46 (1H, AB-X, J=4, 16 Hz), 3.93 (3H, s), 4.73 (2H, s), 5.24 (2H, s), 5.36 (1H, AB-X, J=2, 4 Hz), 5.47 (1H, s), 7.49 (2H, d), 8.09 (1H, s), 8.20 (2H, d)

EXAMPLE 19

Preparation of p-nitrobenzyl 2β-(4,5-dimethoxycarbonyl-1,2,3-triazol-2-yl)methyl-2α-methylpenam-3α-carboxylate A 185 mg quantity of p-nitrobenzyl 2β-chloromethyl-2α-methylpenam-3α-carboxylate, 278 mg of 4,5-dimethoxycarbonyl-1,2,3-triazole and 50 mg of potassium hydrogencarbonate were added to 5 ml of a mixture of acetone and water (3:1), and the mixture was stirred at 30° C. for 16 hours. The reaction mixture was diluted with 15 ml of ethyl acetate, and washed twice respectively with an aqueous solution of sodium hydrogencarbonate and a saturated aqueous solution of sodium chloride. The mixture was dried over anhydrous magnesium sulfate and filtered. The filtrate was condensed under reduced pressure. The residue thus obtained was purified by silica gel column chromatography (eluent: benzene-ethyl acetate=19:1), giving as a first eluate 99 mg of p-nitrobenzyl 2β-(4,5-dimethoxycarbonyl-1,2,3-triazol-2-yl)methyl-2α-methylpenam-3α-carboxylate.

Infrared absorption spectrum (CHCl$_3$) $\nu_{C=O}$ (cm$^{-1}$)=1780, 1747

Nuclear magnetic resonance spectrum (CDCl$_3$) δ (ppm)=1.33 (3H, s), 3.12 (1H, AB-X, J=2, 16 Hz), 3.68 (1H, AB-X, J=4, 16 Hz), 3.93 (6H, s), 4.74 (2H, s), 5.22 (2H, s), 5.15–5.40 (1H, m), 5.37 (1H, s), 7.46 (2H, d), 8.14 (2H, d)

EXAMPLE 20

Preparation of p-nitrobenzyl 2β-(4-p-nitrobenzyloxycarbonyl-1,2,3-triazol-2-yl)methyl-2α-methylpenam-3α-carboxylate Following the general procedure of Example 18 and using appropriate starting materials, 130 mg of p-nitrobenzyl 2β-(4-p-nitrobenzyloxycarbonyl-1,2,3-triazol-2-yl)methyl-2α-methylpenam-3α-carboxylate was obtained as a first eluate.

Infrared absorption spectrum (CHCl$_3$) $\nu_{C=O}$ (cm$^{-1}$)=1780, 1740

Nuclear magnetic resonance spectrum (CDCl$_3$) δ (ppm)=1.32 (3H, s), 3.12 (1H, AB-X, J=2, 16 Hz), 3.66 (1H, AB-X, J=4, 16 Hz), 4.65 (2H, s), 5.22 (2H, s), 5.15–5.50 (2H, m), 5.45 (2H, s) 7.30–8.30 (9H, m)

EXAMPLE 21

The following compounds are prepared according to the same procedure as that of Example 18.
(1) p-nitrobenzyl 2β-(4-p-metylbenzyloxycarbonyl-1,2,3-triazol-2-yl)methyl-2α-methylpenam-30α-carboxylate
(2) p-nitrobenzyl 2β-(4-p-chlorobenzyloxycarbonyl-1,2,3-triazol-2-yl)methyl-2α-methylpenam-3α-carboxylate
(3) p-nitrobenzyl 2α-(4-benzyloxycarbonyl-1,2,3-triazol-2 2-yl)methyl-2α-methylpenam-3α-carboxylate

EXAMPLE 22

Preparation of p-nitrobenzyl 2β-(4-phenyl-1,2,3-triazol-2-yl)methyl-2α-methylpenam-3α-carboxylate Following the general procedure of Example 17 and using appropriate starting materials, 75 mg of 2β-(4-phenyl-1,2,3-triazol-2-yl)methyl-2α-methylpenam-3α-carboxylate was prepared.

Infrared absorption spectrum (CHCl$_3$) $\nu_{C=O}$ (cm$^{-1}$)=1780, 1750 (sh)

Nuclear magnetic resonance spectrum (CDCl$_3$) δ (ppm)=1.30 (3H, s), 3.14 (1H, AB-X, J=2, 16 Hz), 3.65 (1H, AB-X, J=4, 16 Hz), 4.65 (2H, s), 5.15 (2H, s), 5.34 (1H, AB-x, J=2, 4 Hz), 5.65 (1H, s), 7.15–7.90 (7H, m), 7.91 (1H, s), 8.13 (2H, d)

EXAMPLE 23

Preparation of p-nitrobenzyl 2β-(4-formyl-1,2,3-triazol-2-yl)methyl-2α-methylpenam-3α-carboxylate Following the general procedure of Example 17 and using appropriate starting materials, a 76 mg quantity of p-nitrobenzyl 2β-(4-formyl-1,2,3-triazol-2-yl)methyl-2α-methylpenam-3α-carboxylate was prepared.

Infrared absorption spectrum (CHCl$_3$) $\nu_{C=O}$ (cm$^{-1}$)=1780, 1750, 1700

Nuclear magnetic resonance spectrum (CDCl$_3$) δ (ppm)=1.30 (3H, s), 3.12 (1H, AB-X, J=2, 16 Hz), 3.76 (1H, AB-X, J=4, 16 Hz), 4.72 (2H, s), 5.22 (2H, s), 5.33 (1H, AB-X J=2, 4 Hz), 5.45 (1H, s), 7.43 (2H, d), 8.03 (1H, s), 8.15 (2H, d), 10.00 (1H, s)

EXAMPLE 24

Preparation of p-nitrobenzyl 2β-(4,5-dimethoxycarbonyl-1,2,3-triazol-2-yl)methyl-2α-methylpenam-3α-carboxylate 1,1-dioxide A 167 mg quantity of p-nitrobenzyl 2β-(4,5-dimethoxycarbonyl-1,2,3-triazol-2-yl)methyl-2α-methylpenam-3α-carboxylate was dissolved in 3 ml of acetic acid, and 1 ml of water was added. With stirring under ice-cooling 136 mg of potassium permanganate was added thereto. The mixture was then stirred at room temperature for 4 hours. Then, 30% aqueous hydrogen peroxide was further added thereto with stirring under ice-cooling until the mixture became colorless. After addition of water, the reaction mixture was extracted with dichloromethane. Then dichloromethane layer was washed with a saturated aqueous solution of sodium bicarbonate and saturated solution of sodium chloride, and dried over anhydrous sodium sulfate. The solvent was distilled off under reduced pressure, giving 168 mg of p-nitrobenzyl 2β-(4,5-dimethoxycarbonyl-1,2,3-triazol-2-yl)methyl-2α-methylpenam-3α-carboxylate 1,1-dioxide.

Infrared absorption spectrum (Neat) $\nu_{C=O}$ (cm$^{-1}$)=1800, 1760, 1740

Nuclear magnetic resonance spectrum (CDCl$_3$) δ (ppm)=1.40 (3H, s), 3.57 (2H, d, J=3 Hz), 3.98 (6H, s), 4.67 (1H, t, J=3 Hz), 5.05 (3H, s), 5.22 (2H, s), 7.48 (2H, d), 8.21 (2H, d)

EXAMPLE 25

Preparation of p-nitrobenzyl 2β-(4-p-nitrobenzyloxycarbonyl-1,2,3-triazol-2-yl)methyl-2α-methylpenam-3α-carboxylate 1-oxide A 41 mg quantity of p-nitrobenzyl 2β-(4-p-nitrobenzyloxycarbonyl-1,2,3-triazol-2-yl)methyl-2α-methylpenam-3α-carboxylate, 16 μl of aqueous hydrogen peroxide and 10 mg of formic acid were stirred in 0.4 ml of methylene chloride at room temperature for 2.5 hours. The mixture was washed with water and dried over magnesium sulfate. The methylene chloride was distilled off under reduced pressure. The residue was subjected to silica gel column chromatography (eluent: benzene-ethyl acetate=19:1), giving 40 mg of p-nitrobenzyl 2β-(4-p-nitrobenzyloxycarbonyl-1,2,3-triazol-2-yl)methyl-2α-methylpenam-3α-carboxylate 1-oxide.

Infrared absorption spectrum (CHCl$_3$) $\nu_{C=O}$ (cm$^{-1}$)=1782, 1740

Nuclear magnetic resonance spectrum (CDCl$_3$) δ (ppm)=0.86 (3H, s), 3.42–3.46 (2H, m), 4.67 (1H, s), 4.82–4.97 (1H, m), 5.12 and 5.32 (each 1H, AB, J=14, 7 Hz), 5.37 (2H, d, J=2.6 Hz), 5.50 (2H, s), 7.63 (4H, d, J=9 Hz), 8.16 (1H, s), 8.26 (2H, d, J=9 Hz), 8.28 (2H, d, J=9 Hz)

Given below are examples of preparation of the present antibacterial compositions.

| Preparation Example 1 | |
|---|---|
| Ampicillin | 200 mg |
| Sodium 2α-methyl-2β-(1,2,3-triazol-2-yl)methylpenam-3α-carboxylate 1,1-dioxide | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

| Preparation Example 2 | |
|---|---|
| Amoxycillin | 100 mg |
| Sodium 2α-methyl-2β-(1,2,4-triazol-1-yl)methylpenam-3α-carboxylate 1,1-dioxide) | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

| Preparation Example 3 | |
|---|---|
| Pivmecillinam | 70 mg |
| Sodium 2α-methyl-2β-(1,2,4-triazol-1-yl)methylpenam-3α-carboxylate 1-1-dioxide) | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |

-continued

| Preparation Example 3 | | |
|---|---|---|
| | Total | 220 mg (amount per tablet) |

The above ingredients are formulated in the proportions listed above into a tablet.

| Preparation Example 4 | |
|---|---|
| Sodium 2α-methyl-2β-(1,2,3-triazol-2-yl)methylpenam-3α-carboxylate 1,1-dioxide | 120 mg |
| Hydroxypropyl cellulose | 3 mg |
| Corn starch | 25 mg |
| Magnesium stearate | 2 mg |
| Total | 150 mg (amount per tablet) |

The above ingredients are formulated in the proportions listed above into a tablet.

The compounds obtained in some of the foregoing examples were studied for the antibacterial activity.

Test for Antibacterial Activity

The minimal inhibitory concentration (MIC) of piperacillin in the presence of 5 μg/ml of the compounds of the present invention against various bacteria were determined by the MIC assay method of Japan Society of Chemotherapy (Chemotherapy 29(1), pp. 76–79, 1981).

The MIC value of the various compounds according to the invention and piperacillin, as used singly, were also determined. Each test strain was grown on Mueller Hinton Medium (Difco) and used for inoculation after dilution to concentration of $10^6$ CFU/ml. The assay media (Mueller Hintoon Medium) containing piperacillin and the compound of the invention in a series of concentrations were inoculated with the test strain and incubated at 37° C. for 20 hours.

The minimum concentration at which no more than 5 colonies were observed was determined. The results are shown in Table 1. Though not shown, the MIC value of the test compounds according to the invention, as used singly, were invariably not less than 25 μg/ml. All the test strains used in the above assay were β-lactamase producers.

TABLE 1

| | MIC (μg/ml) | | | |
|---|---|---|---|---|
| | | piperacillin plus the present compound | | |
| Test Strain | piperacillin alone | Example 4 | Example 14 | Example 16 |
| E. coli SHV1 | 25 | 0.78 | 0.78 | 0.78 |
| E. coli TEM1 | 100 | 0.78 | 0.78 | 0.78 |
| E. coli 1573E | 6.25 | 1.56 | 0.78 | 1.56 |
| E. coli OXA3 | 3.13 | 0.78 | 0.78 | 0.78 |
| K. pneumoniae 101L | 100 | 0.78 | 1.56 | 1.56 |
| P. mirabillis 60 | 1.56 | 0.20 | 0.20 | 0.20 |
| Serratia 200L | 25 | 0.78 | 0.78 | 0.78 |
| Citrobacter 2046E | 25 | 0.78 | 0.78 | 0.78 |
| Citrobacter 962L | 100 | 3.13 | 3.13 | 3.13 |
| P. aeruginosa PSE3 | 50 | 6.25 | 6.25 | 6.25 |
| P. aeruginosa PSE4 | 200 | 50 | 50 | 25 |
| S. aureus 54K | 3.13 | 0.78 | 0.78 | 0.78 |

We claim:

1. A 2β-substituted-methylpenicillanic acid compound of the formula

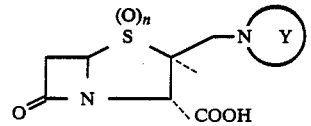

(I)

wherein n is 0, 1 or 2, and

is imidazolyl, pyrazolyl, tetrazolyl, 1,2,3-triazol-2-yl, 1,2,4-trialzolyl, benzotriazolyl or benzimidazolyl, each of which may be optionally substituted with alkyl, alkoxycarbonyl, phenyl, formyl or benzyloxycarbonyl which may optionally have alkyl, nitro or a halogen atom on the benzene ring; a pharmaceutically acceptable salt thereof; or an ester thereof formed by protecting the carboxyl group at the 3-position of the compound of the formula (I) by a protective group selected from the class consisting of lower alkyl, lower alkoxymethyl, lower alkylcarbonyloxy-lower alkyl, ($C_{5-7}$ cycloalkyl)carbonyloxy-lower alkyl, benzylcarbonyloxy-lower alkyl, benzoyloxy-lower alkyl, 3-phthalidyl, crotonolacton-4-yl, γ-butyrolacton-4-yl, halogenated lower alkyl substituted with 1 to 3 halogen atoms, methyl group which is substituted with 1 or 2 phenyl groups optionally having lower alkoxy or nitro on the benzene ring, tetrahydropyranyl, dimethylaminoethyl, dimethylchlorosilyl, trichlorosilyl, tert-butylsilyl and (5-substituted or unsubstituted-2-oxo-1,3-dioxoden-4-yl)methyl.

2. A compound as defined in claim 1 wherein n is 2; a pharmaceutically acceptable salt thereof; or an ester thereof formed by protecting the carboxyl group at the 3-position of the compound of the formula (I) by a protective group selected from the class consisting of lower alkyl, lower alkoxymethyl, lower alkylcarbonyloxy-lower alkyl, ($C_{5-7}$ cycloalkyl)carbonyloxy-lower alkyl, benzylcarbonyloxy-lower alkyl, benzoyloxy-lower alkyl, 3-phthalidyl, crotonolacton-4-oyl, γ-butyrolacton-4-yl, halogenated lower alkyl substituted with 1 to 3 halogen atoms, methyl group which is substituted with 1 or 2 phenyl groups optionally having lower alkoxy or nitro on the benzene ring, tetrahydropyranyl, dimethylaminoethyl, dimethylchlorosilyl, trichlorosilyl, tertbutylsilyl and (5-substituted or unsubstituted-2-oxo-1, 3-dioxoden-4-yl)methyl.

3. A compound as defined in claim 1 wherein the pharmaceutically acceptable salt is an alkali metal salt, alkaline earth metal salt, ammonium salt, cyclohexylamine salt, trimethylamine salt, diethanolamine salt, arginine salt or lysine salt of the compound of the formula (I).

4. A compound as defined in claim 1 wherein the group

is imidazolyl, pyrazolyl, tetrazolyl, 1,2,3-triazol-2-yl, 2,2,4-triazolyl, benzotriazolyl or benzimidazolyl, each of which may optionally have 1 to 3 substituents, said substituents being selected from the group consisting of alkyl, alkoxycarbonyl, phenyl, formyl and benzyloxycarbonyl which may optionally have 1 to 3 substituents selected from the group consisting of $C_1-C_6$ alkyl, nitro and halogen atom on the benzene ring; a pharmaceutically acceptable salt thereof; or an ester thereof formed by protecting the carboxyl group at the 3-position of the compound of the formula (I) by a protective group selected from cycloalkyl)-carbonyloxy-lower alkyl, phthalidyl γ-butyrolacton-4-yl and (5-substituted or unsubstituted-2-oxo-1,3-dioxoden-4-yl)methyl.

5. A compound as defined in claim 1 wherein the group

is 1,2,3-triazol-2-yl; a pharmaceutically acceptable salt thereof; or an ester thereof formed by protecting the carboxyl group at the 3-position of the compound of the formula (I) by a protective group selected from the class consisting of lower alkylcarbonyloxy-lower alkyl, ($C_{5-7}$ cycloalkyl)carbonyloxy-lower alkyl, phthalidyl, γ-butyrolacton-4-yl and (5-substituted or unsubstituted-2-oxo-1,3-dioxoden-4-yl)methyl.

6. A compound as defined in claim 1 wherein the group

is imidazol-lyl; a pharmaceutically acceptable salt thereof; or an ester thereof formed by protecting the carboxyl group at the 3-position of the compound of the formula (I) by a protective group selected from the class consisting of lower alkylcarbonyloxy-lower alkyl, ($C_{5-7}$ cycloalkyl)carbonyloxy-lower alkyl, phthalidyl, γ-butyrolacton-4-yl and (5-substituted or unsubstituted-2-oxo-1,3-dioxoden-4-yl)methyl.

7. A compound as defined in claim 1 which is sodium 2α-methyl-2β-(1,2,3-triazol-2-yl)methylpenam-3α-carboxylate 1,1-dioxide.

8. A compound as defined in claim 1 which is sodium 2β-(imidazol-1-yl)methyl-2α-methylpenam-3α-carboxylate 1,1-dioxide.

9. A pharmaceutical composition for treating bacterial infections in mammals which comprises (a) a β-lactam antibiotic, (b) a penicillanic acid compound of the formula

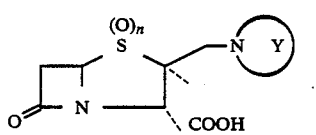

wherein n is 0, 1 or 2, and

is imidazolyl, pyrazolyl, tetrazolyl, 1,2,3-triazol-2-yl, 1,2,4-triazolyl, benzotriazolyl or benzimidazolyl, each of which may be optionally substituted with alkyl, alkoxycarbonyl, phenyl, formyl or benzyloxycarbonyl which may optionally have alkyl, nitro or a halogen atom on the benzene ring; a pharmaceutically acceptable salt thereof; or an ester thereof formed by protecting the carboxyl group at the 3-position of the compound of the formula (I) by a protective group selected from the class consisting of lower alkylcarbonyloxy lower alkyl, ($C_{5-7}$ cycloalkyl)-carbonyloxy-lower alkyl, phthalidyl, γ-butyrolacton-4-yl and (5-substituted or unsubstituted-2-oxo-1,3-dioxoden-4-yl)methyl, and (c) a pharmaceutically acceptable, non-toxic carrier or excipient therefor.

10. A pharmaceutical composition as defined in claim 9 wherein n is 2.

11. A pharmaceutical composition as defined in claim 9 wherein the pharmaceutically acceptable salt is an alkali metal salt, alkaline earth metal salt, ammonium salt, cyclohexylamine salt, trimethylamine salt, diethanolamine salt, arginine salt or lysine salt of the compound of the formula (I).

12. A pharmaceutical composition as defined in claim 9 wherein the group

is imidazolyl, pyrazolyl, tetrazolyl, 1,2,3-triazol-2-yl, 1,2,4-triazolyl, benzotriazolyl or benzimidazolyl, each of which may optionally have 1 to 3 substituents, said substituents being selected from the group consisting of alkyl, alkoxycarbonyl, phenyl, formyl and benzyloxycarbonyl which may optionally have 1 to 3 substituents selected from the group consisting of $C_1-C_6$ alkyl, nitro and halogen atom on the benzene ring.

13. A pharmaceutical composition as defined in claim 9 wherein the group

is imidazolyl, pyrazolyl, tetrazolyl, 1,2,3-triazol-2-yl, 1,2,4-triazolyl, benzotriazolyl or benzimidazolyl, each of which may be optionally be substituted with 1 to 3 substituents selected from the group consisting of $C_1-C_6$ alkyl, nitro and halogen atom on the benzene ring.

14. A pharmaceutical composition as defined in claim 9 wherein the group is 1,2,3-triazol-2-yl.

15. A pharmaceutical composition as defined in claim 9 wherein the group $-N\underset{}{\bigcirc}Y$ is imidazol-1-yl group.

16. A pharmaceutical composition as defined in claim 9 wherein the weight ratio of (a)/(b) is about 0.1 to about 10.

17. A pharmaceutical composition as defined in claim 9 wherein the weight ratio of (a)/(b) is about 0.2 to about 5.

18. A method of treating a bacterial infection in a patient in need of such treatment comprising administering to said patient an effective amount of the composition of claim 9.

19. A pharmaceutical composition for inhibiting β-lactamase comprising an effective amount of at least one of the compound and salt and ester thereof as defined in claim 1 in combination with a pharmaceutically acceptable carrier or excipient therefor.

* * * * *